United States Patent
Kai et al.

(10) Patent No.: US 6,773,710 B2
(45) Date of Patent: Aug. 10, 2004

(54) RECOMBINANT CANINE DISTEMPER VIRUS VACCINE AGAINST CANINE DISTEMPER AND LEISHMANIASIS

(75) Inventors: Chieko Kai, Tokyo (JP); Ryuichi Miura, Tokyo (JP); Yoshitsugu Matsumoto, Tokyo (JP)

(73) Assignee: Nippon Biologicals, Inc., Tokyo (JP)

( * ) Notice: Subject to any disclaimer, the term of this patent is extended or adjusted under 35 U.S.C. 154(b) by 0 days.

(21) Appl. No.: 10/265,176

(22) Filed: Oct. 4, 2002

(65) Prior Publication Data

US 2003/0190330 A1 Oct. 9, 2003

(30) Foreign Application Priority Data

Apr. 5, 2002 (JP) ........................................ 2002-103924

(51) Int. Cl.⁷ .............................................. A61K 39/12
(52) U.S. Cl. ................................ 424/199.1; 424/204.1; 435/320.1; 435/69.1
(58) Field of Search ........................... 424/199.1, 204.1, 424/213.1, 184.1; 435/320.1, 235.1, 69.1; 536/23.72

(56) References Cited

FOREIGN PATENT DOCUMENTS

| JP | 2001-275684 | | 10/2001 |
|---|---|---|---|
| WO | WO 02/00883 | * | 1/2002 |

OTHER PUBLICATIONS

Gurunathan et al , The Journal of Experimental Medicine, Oct. 6, 1997, No. 7, vol. 186, pp. 1137–1147.*

* cited by examiner

Primary Examiner—Ali R. Salimi
(74) Attorney, Agent, or Firm—Webb Ziesenheim Logsdon Orkin & Hanson P.C.

(57) ABSTRACT

The present invention provides a vaccine against canine distemper and leishmaniasis by constructing a recombinant canine distemper virus containing a gene encoding a protein associated with protection against Leishmania protozoa infection inserted into the canine distemper virus vector.

2 Claims, 5 Drawing Sheets

SEQUENCE LISTING

```
<160> NUMBER OF SEQ ID NOS: 2

<210> SEQ ID NO 1
<211> LENGTH: 74
<212> TYPE: DNA
<213> ORGANISM: Artificial Sequence
<220> FEATURE:
<223> OTHER INFORMATION: Description of Artificial Sequence: Primer

<400> SEQUENCE: 1
taaggccggc ctctaaactc attataaaaa acttagggct caggtagtcc aacaatgaac      60
tacgagggtc acct                                                       74

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 2
tcgaggccgg ccttactcgg cgtcggagat g                                    31
```

RECOMBINANT CANINE DISTEMPER VIRUS VACCINE AGAINST CANINE DISTEMPER AND LEISHMANIASIS

BACKGROUND OF THE INVENTION

1. Field of the Invention

The present invention relates to a recombinant canine distemper virus which is useful as a vaccine against canine distemper and leishmaniasis, a vaccine comprising the recombinant virus, and an antiserum obtained from an animal inoculated with the vaccine.

2. Description of the Prior Art

Canine distemper occurs naturally in animals such as the families Canidae and Mustelidae. It is characterized by symptoms such as fever, respiratory disorders such as pneumonia and bronchitis, diarrhea and nervous disorders. This disease is one of the representative infectious diseases in canines. It has been controlled for about thirty years by inoculation with live vaccines, but recently it has been reported that the occurrence of this disease is increasing worldwide, including in Japan. Even vaccinated dogs sometimes develop the disease, indicating that there is a possibility that the prior art vaccination cannot completely control the currently widespread field isolates. It has been reported that when examining the cross neutralizing reaction of the serum obtained from infected dogs against the vaccine strain, the reactivity against the vaccine strain was low. Recently isolated field isolates have mutations in the H gene encoding membrane protein, which is important for infection. Dogs are used as an experimental animal for physiological or pharmaceutical studies, as a disease model for humans, and for studies of infectious diseases, and they are recognized to be useful to industry. Also, dogs have played an important role in the social life of humans as domestic animals for thousands of years. Therefore, the protection of dogs from canine distemper is desired eagerly in many fields.

Canine Distemper Virus (CDV) that causes canine distemper belongs to the genus Morbillivirus of the family Paramyxoviridae. The canine distemper virus particle is pleomorphic, and has the genomic RNA which does not serve as a template for translation, namely a negative single strand RNA, surrounded by an envelope of 150–200 nm in diameter.

The present inventors established a system for reconstituting the canine distemper virus, which system is necessary for gene manipulation of the virus (see Japanese Patent Application Kokai (Laid Open) No. 2001-275684). However, there remains a need for a multivalent vaccine against canine distemper virus and other pathogens to be actually prepared and for the efficacy thereof to be confirmed.

On the other hand, leishmaniasis is a zoonosis in humans and animals caused by Leishmania protozoa belonging to hemoflagellates, and it is designated as one of the infectious diseases which the World Health Organization intends to eradicate. The number of persons infected with this disease is estimated at about 12 million, and every year two million persons will be infected with this disease in 88 countries. Leishmaniasis is generally classified into three types of diseases, 1) visceral leishmaniasis, 2) cutaneous leishmaniasis, and 3) mucocutaneous leishmaniasis, and each is characterized by 1) abdominal symptoms such as splenohepatomegaly and diarrhea, anemia and leukopenia, 2) induration or tuberculation and ulceration of the skin, and 3) tissue destruction of the nasal septum, labia oris, palate, pharynx etc. Infection of humans occurs by entry of humans into the life cycle of the vector insect, sand fly, and dogs and wild canines or rodents acting as a host. Effective prophylaxis or therapy has not been developed. It has been reported that the elimination of the infection in dogs will allow the control of the infection of humans epidemiologically. Therefore, the development of vaccines or a method for prevention of the protozoa is expected to lead to the eradication of this infectious disease not only in the veterinary field but also in humans.

As mentioned above, there is currently no effective vaccine against leishimaniasis. Leishmania antigens such as LACK (Leishmania homologues receptors for activated C kinase), A2 and Promastigote Surface Protease (gp63) expressed in Leishmania are known as a target antigen for suppressing the propagation of Leishmania protozoa, and thereby promoting the cure of leishmaniasis. It is effective for protection against leishmaniasis to induce protective Th1 immune responses after the infection. A DNA vaccine which is characterized in that the LACK gene linked to a suitable transcriptional control sequence is inoculated directly into the body, and a recombinant vaccinia virus vaccine containing such a LACK gene have been reported to be effective in a vaccination experiment in mice and to be particularly more effective when used along with IL-12. A2 is one of the major antigen proteins expressed specifically to amastigotes of Leishmania protozoa (*L. donovani*) causing visceral leishmaniasis and is associated with the pathogenicity of leishmaniasis. In the vaccination experiment in mice, it has been reported that the inoculation of A2 leads to induction of protective Th1 immune responses. However, such vaccines are in the development stage and at present cannot be used practically.

SUMMARY OF THE INVENTION

The object of the present invention is to provide a recombinant bivalent virus vaccine which is effective to protect against canine distemper and leishmaniasis and allows a simple procedure in vaccination.

The present inventors noticed that since canine distemper virus grows essentially in a dog as a host and the vaccine comprising the virus induces an effective immune response and gives permanent immunity, the virus can be used as a virus vaccine vector, and they tried to construct recombinant canine distemper virus having a foreign gene involved in the prevention of the infection of Leishmania protozoa inserted therein. They found that the resulting recombinant canine distemper virus is effective as a vaccine against both canine distemper and leishmaniasis.

Thus, the present invention provides recombinant canine distemper virus containing a gene encoding a protein involved in protection against leishmaniasis inserted into the canine distemper virus genome.

The present invention also provides recombinant canine distemper virus which has the infectivity, and is capable of expressing a protein which leads to protection against leishmaniasis after vaccination with the recombinant virus within infected cells.

Furthermore, the present invention relates to the above-mentioned recombinant canine distemper viruses wherein at least one gene of the canine distemper virus genome, particulary a gene encoding a functional protein of canine distemper virus, is modified.

The above-mentioned recombinant canine distemper virus may contain at least one foreign gene in addition to a gene encoding a protein concerned with protection against leishmaniasis.

The present invention also relates to a bivalent vaccine against canine distemper virus and leishmaniasis, comprising the above-mentioned recombinant canine distemper virus. Furthermore, the present invention relates to an antiserum obtainable from bodily fluid which is recovered from the animal infected with the above-mentioned recombinant canine distemper virus.

DETAILED DESCRIPTION OF THE INVENTION

The recombinant canine distemper virus of the present invention is characterized in that a gene encoding a protein concerned with protection against leishmaniasis infection is inserted into the viral genome.

The recombinant canine distemper virus of the present invention may be prepared by using the method for reconstituting canine distemper virus described in Japanese Patent Application Kokai (Laid-Open) No. 2001-275684. For example, the recombinant cDNA comprising cDNA of the canine distemper virus genome having a desired foreign gene incorporated therein may be constructed. Then, this recombinant cDNA may be introduced into a cell expressing genes relating to transcription and replication along with a unit capable of intracellularly transcribing RNA from the cDNA as a template to reconstitute canine distemper virus particles.

Canine distemper virus for use in preparing the recombinant canine distemper virus may be a canine distemper virus capable of inducing a high level of neutralizing antibodies against field canine distemper virus. Examples of the canine distemper viruses include strain Yanaka and strain Hamamatsu. Vaccine strains such as strain Onderstepoort may be used as long as this strain is modified by genetic engineering so as to induce the corresponding neutralizing antibodies.

Genes of Leishmania protozoa to be inserted as a foreign gene into canine distemper virus genome may be genes encoding proteins which lead to protection against leishmaniasis and are exemplified by a gene encoding a protein concerned with pathogenicity or propagation of Leishmania protozoa, this protein being capable of inducing an immune response when expressed within the body. Such genes include, but are not limited to, LACK (Leishmania homologues receptors for activated C kinase) gene, A2 gene, gp63, TSA gene, LmSYII gene of Leishmania protozoa, and PSA-2 of Leishmania protozoa.

The sequences of LACK gene and A2 gene are known by AF034793 and S69693 of Genebank database, respectively. Therefore, cDNA of LACK gene or A2 gene can be obtained from RNA extracted from Leishmania protozoa using primers designed based on the known sequences.

The genome of canine distemper virus has a leader sequence and a trailer sequence at each end and N, P, M, F, H and L genes encoding viral structural proteins between the leader sequence and the trailer sequence. N protein packages the viral RNA by binding the RNA sequentially from the 3' terminus. P gene produces P, V and C proteins. P protein is known to serve as a small subunit of RNA polymerase and participate in viral transcription and replication. L protein functions as a large subunit of RNA polymerase. M protein supports the structure of the viral particle from within, and F and H proteins are concerned with the invasiveness into a host cell.

In preparing the recombinant canine distemper virus of the present invention, genomic RNA may be prepared from canine distemper virus as mentioned above and cDNA thereof may be obtained by any conventional procedure. The cDNA may be liked downstream of a particular promoter. Depending on an orientation of the cDNA, genomic RNA or cRNA may be transcribed. The above-mentioned cDNA of a gene of Leishmania protozoa may be inserted into the cDNA of the canine distemper virus by genetic engineering techniques to construct a recombinant cDNA.

The recombinant canine distemper virus of the present invention may have any other foreign gene inserted at any site of viral RNA contained in the recombinant, or it may have any genome gene deleted or modified, as long as the recombinant maintains its infectivity and is effective for the protection against Leishmania protozoa infection. Other foreign genes to be inserted are exemplified by genes encoding various proteins relating to pathogenicity of a virus, bacterium or parasite, genes encoding various cytokines, and peptide hormones which can be expressed within hosts. Expression level of the inserted foreign gene can be controlled by the site of gene insertion, or the sequences of RNA flanking the foreign gene. Also, for example, the genes related to immunogenicity may be modified so as to decrease the infectivity of the virus and proliferation rate of the virus.

Preferably, in preparing cDNA of the canine distemper virus genome, restriction enzyme sites are placed between two genes of N, P, M, F, H and L genes encoding proteins which constitute the virus. This facilitates the insertion of the desired foreign gene and allows the selection of the site of the optimal expression of a foreign gene.

The recombinant virus can be produced by introducing the cDNA of canine distemper virus genome obtained by gene manipulation as mentioned above and a unit capable of intracellularly transcribing RNA from this DNA as a template into a host expressing all enzymes for transcription and replication of canine distemper virus or closely related viruses. For example, the unit capable of transcribing RNA may be a DNA molecule expressing a DNA-dependent RNA polymerase acting on a particular promoter, and the above-mentioned cDNA obtained by gene manipulation linked downstream of this particular promoter. Specific examples of such a unit include recombinant vaccinia virus expressing T7 RNA polymerase, and a cultured cell having T7 RNA polymerase gene incorporated artificially.

The host into which the cDNA is introduced along with the above-mentioned unit may be a host cell expressing all enzymes for the transcription and replication of canine distemper virus or closely allied viruses, i.e., a host cell simultaneously expressing N, P and L proteins, or their equivalents. For example, a cell having genes encoding these proteins on its chromosome, or a suitable cell carrying plasmids, each plasmid having a gene encoding N, P, and L protein may be used. Preferably, 293 cell line or B95 cell line having incorporated therein suitable plasmids, each plasmid containing gene encoding N, P and L proteins, is used.

The recombinant canine distemper virus of the present invention obtained as mentioned above contains a gene encoding a protein which leads to protection against leishmaniasis. As demonstrated in the following Examples this gene expresses a protein which leads to protection against leishmaniasis after the inoculation of the recombinant virus within the infected cells, resulting in an inhibitory effect on the proliferation of Leishmania protozoa. Additionally, this recombinant virus retains a function as a canine distemper virus and is effective as a vaccine against canine distemper.

Thus, the inoculation of a single vaccine of recombinant canine distemper virus enables protection from canine distemper and leishmaniasis infectious diseases. In the preparation of the vaccine, any conventionally used adjuvants and additives may be added.

Furthermore, an antiserum etc. may be obtained by infecting animals with the above-mentioned recombinant canine distemper virus and recovering bodily fluid. The resulting antiserum or the like can be used for treatment or diagnosis of the diseases.

The present invention is illustrated by the following examples, but is not limited thereto.

EXAMPLES

Example 1
Construction of Recombinant Canine Distemper Virus Containing LACK Gene (CDV-LACK)

Figure 1:
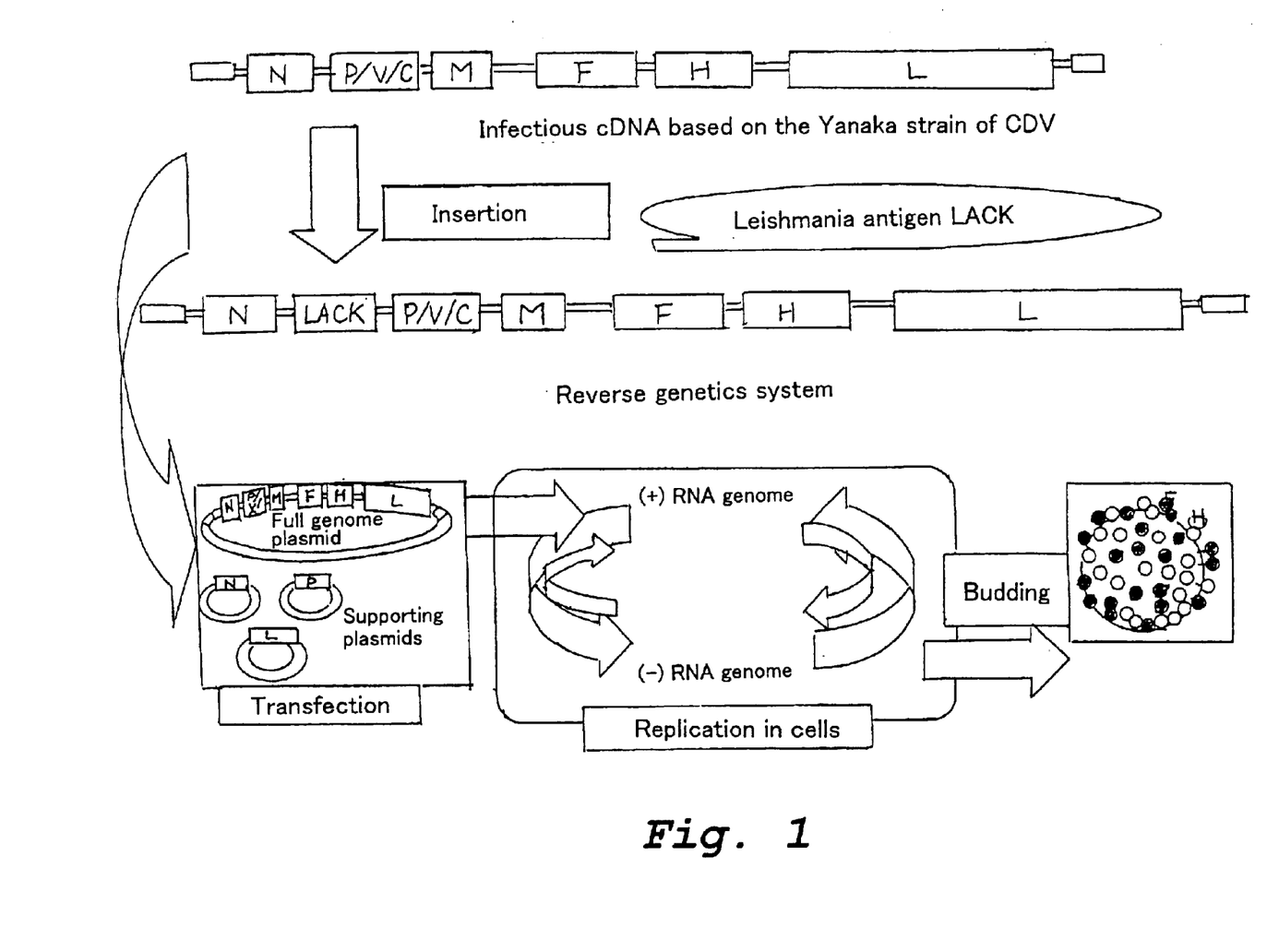
FIG. 1 is a scheme for construction of pCDV(5+)-LACK.

As an infectious cDNA clone required for the construction of recombinant CDV, pCDV (5+), which is based on the sequence of the whole genome of a field isolate of canine distemper virus, strain Yanaka, and contains artificial restriction sites at both ends of each of six genes encoding viral structural proteins was used. LACK cDNA was obtained by RT-PCR using whole RNA extracted from Leishmania protozoa (*L. donovani*). The obtained LACK cDNA was further amplified with primers (SEQ ID Nos. 1 and 2) containing Fse I restriction sequence and was examined for its sequence after being cloned in a plasmid vector. This plasmid was digested with Fse I to produce LACK cDNA, which was then inserted at the Fse I site between the N gene and P gene of pCDV (5+) to obtain infectious cDNA clone, pCDV (5+)-LACK, which was used to construct recombinant canine distemper virus containing LACK gene. A scheme for construction of pCDV (5+)-LACK is shown in FIG. 1.

Primer Sequences

SEQ ID No. 1: 5'-taaggccggcctctaaactcattataaaaaacttagggctcaggtagtccaacaatgaactacgagggtcacct-3'

SEQ ID No. 2: 5'-tcgaggccggccttactcggcgtcggagatg-3'

Reconstitution of recombinant canine distemper virus particles was conducted as follows.

293 Cells (1,000,000 cells/well) trypsinized in a usual manner were placed in a 6-well plate and incubated in Dulbecco-MEM medium (2 ml) supplemented with 5% fetal bovine serum in a 5% $CO_2$ atmosphere at 37° C. for 24 hours. After the medium was removed, a suspension of recombinant vaccinia virus MVA-7 expressing T7 RNA polymerase in PBS (0.2 ml) was added to the well at a multiplicity of infection (moi) of 2. The plate was gently shaken every 10 minutes to thoroughly spread the viral suspension for 30 min infection. After removing the virus suspension and adding 2 ml of a medium to the well, 100 µl of cDNA solution were added dropwise. The cDNA solution had been prepared as follows.

Plasmids pGEM-NP, pGEM-P and pGEM-L, which were for the replication of canine distemper virus, were placed in a 1.5-ml sampling tube in an amount of 1 µg, 1 µg and 0.1 µg, respectively. To this tube were added 1 µg of pCDV (5+)-LACK and sterilized distilled water to obtain 10 µl of nucleic acid solution. Separately, 0.17 ml of Dulbecco-MEM medium were placed in another sampling tube. To this tube were added 20 µl of Fugene 6 (Boehringer Mannheim) dropwise, and the mixture was left standing as such at room temperature for 15 minutes. This solution was mixed with the nucleic acid solution, and the mixture was left standing at room temperature for an additional 10 minutes to obtain a cDNA solution. 100 µl of the cDNA solution were added to the medium in the well and agitated gently.

The plate containing the above-described well was incubated in a 5% $CO_2$ atmosphere at 37° C. for 72 hours. Then, 1 ml of the medium was removed from the well, and the plate was frozen at −80° C. for 3 hours. The plate was then thawed to room temperature to obtain a suspension containing cell lysate.

Previously, B95a cells (1,000,000 cells/well) and RPMI 1640 medium supplemented with 5% fetal bovine serum were placed in each well of a 6-well plate. To each well were added 400 µl of the suspension of cell lysate dropwise. The plate was incubated in a 50% $CO_2$ atmosphere at 37° C. for 24 hours, and after exchange of the medium with RPMI 1640 medium supplemented with 5% fetal bovine serum, it was further incubated under the same condition for 72 hours.

Figure 2:
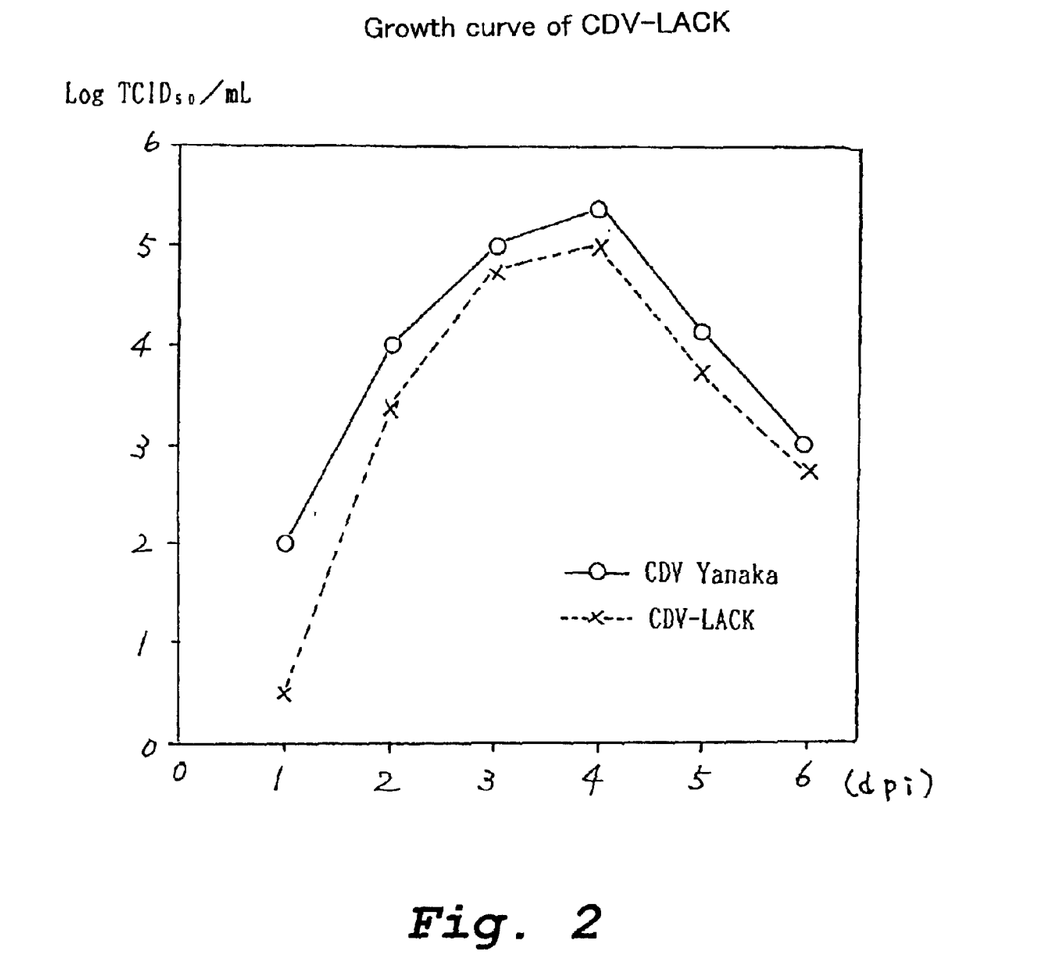
FIG. 2 is a growth curve of CDV-LACK in B95a cells.

The reconstitution of canine distemper virus particles was confirmed by the appearance of cytopathogenic effect (CPE) as an indicator, which effect is observed in B95a cells when infected with canine distemper virus. It was confirmed by RT-PCR that the recovered viruses were canine distemper viruses containing the LACK gene inserted therein (CD V-LACK). FIG. 2 shows the growth curve of CD V-LACK in B95a cells. There was no significant difference between the growth of CD V-LACK and that of strain Yanaka of CDV (parent strain).

Example 2
Evaluation of Expression of LACK Protein in Cells Infected with CDV-LACK The expression of the LACK protein in the infected cells was confirmed by the indirect fluorescent antibody technique as follows.

B95a cells cultured on a 24-well plate were infected with CDV-LACK at a multiplicity of infection (moi) of 0.01. On Day 3, the cells were fixed with 3% paraformaldehyde dissolved in PBS for 15 minutes, washed once with a sufficient amount of PBS for 5 minutes, and treated with 5% Triton-X100 in PBS for 5 minutes and washed three times with PBS for 5 minutes each time. Then, diluted ascites of a mouse immunized with LACK expressed in *E. coli* were used as the first antibody. Simultaneously, CDV-N monoclonal antibody diluted 500 times was used as a control. Each reaction was carried out at room temperature for 1 hour. After washing three times with PBS for 10 minutes, the reaction with anti-mouse IgG antibodies labeled with FITC as the second antibody was conducted at room temperature for 1 hour, followed by washing three times with PBS containing 0.2% Tween 20 for 15 minutes.

The treated cells were observed under a confocal microscope. LACK protein was confirmed to be expressed in the cells infected with CDV-LACK.

Example 3
Protection of Dogs from Canine Distemper in Experimental Vaccination with CDV-LACK The effect of CDV-LACK inoculation on prevention against canine distemper was examined as follows.

4-week old beagles were used in the infection experiment. Two dogs in the CDV-LACK inoculated group were inoculated with $10^{4.5}$ $TCID_{50}$ of virus, and two dogs in the mock group were inoculated with 500 µl of PBS subcutaneously. After two weeks, a second inoculation was carried out in the same way as for the first inoculation. On Week 3 after the first inoculation, the dogs were challenged with virulent CDV strain, Snyder-Hill, intracerebrally (500 µl of 10% brain homogenate infected with the virulent CDV). The dogs were examined with respect to body weight, body temperature, number of leukocytes, clinical conditions and production of antibodies.

Figure 3:
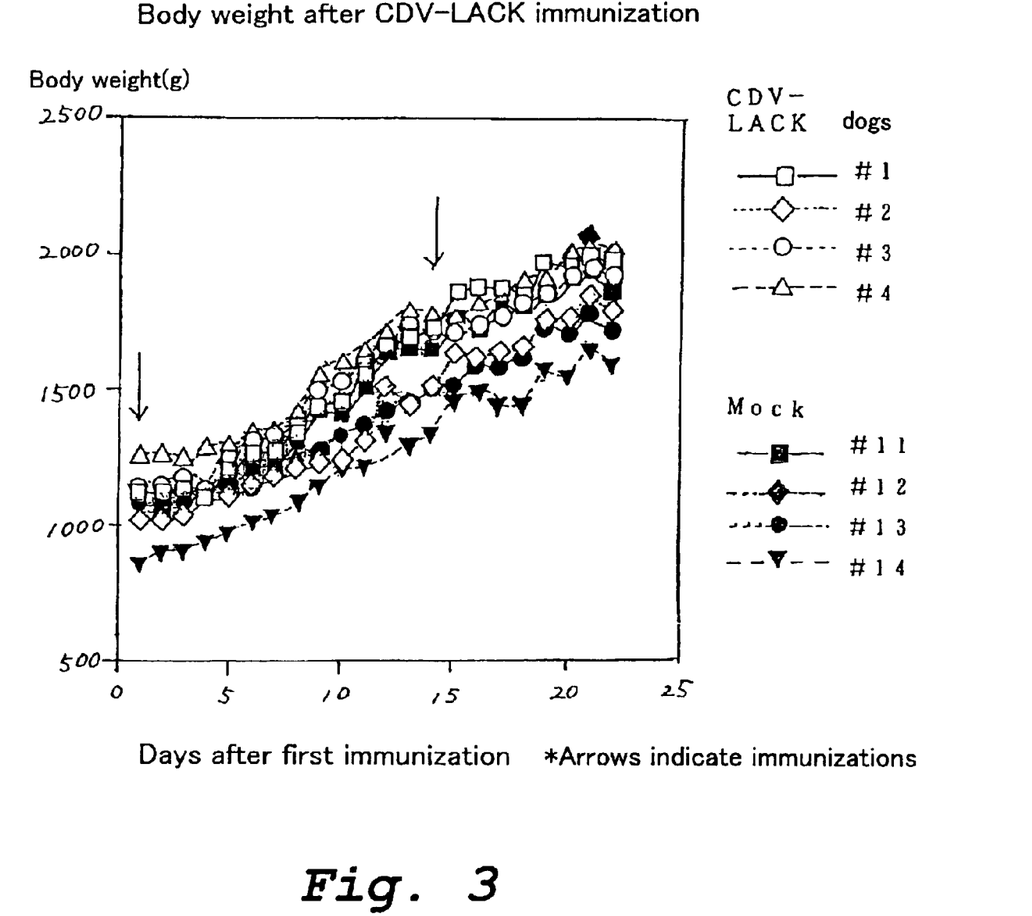
FIG. 3 shows the change in body weight of test animals after vaccination with CDV-LACK.

FIG. 3 shows the change in body weight of the test animals during the three weeks after the first inoculation of CDV-LACK. Anti-CDV antibodies were determined by ELISA using CDV-infected cells as an antigen. The antibody titer increased after two weeks in the CDV-LACK inoculated group. In this group, there was no significant change in body weight, body temperature, number of leukocytes, or conditions of the dogs, and therefore, it became apparent that CDV-LACK itself is not pathogenic.

Figure 4:
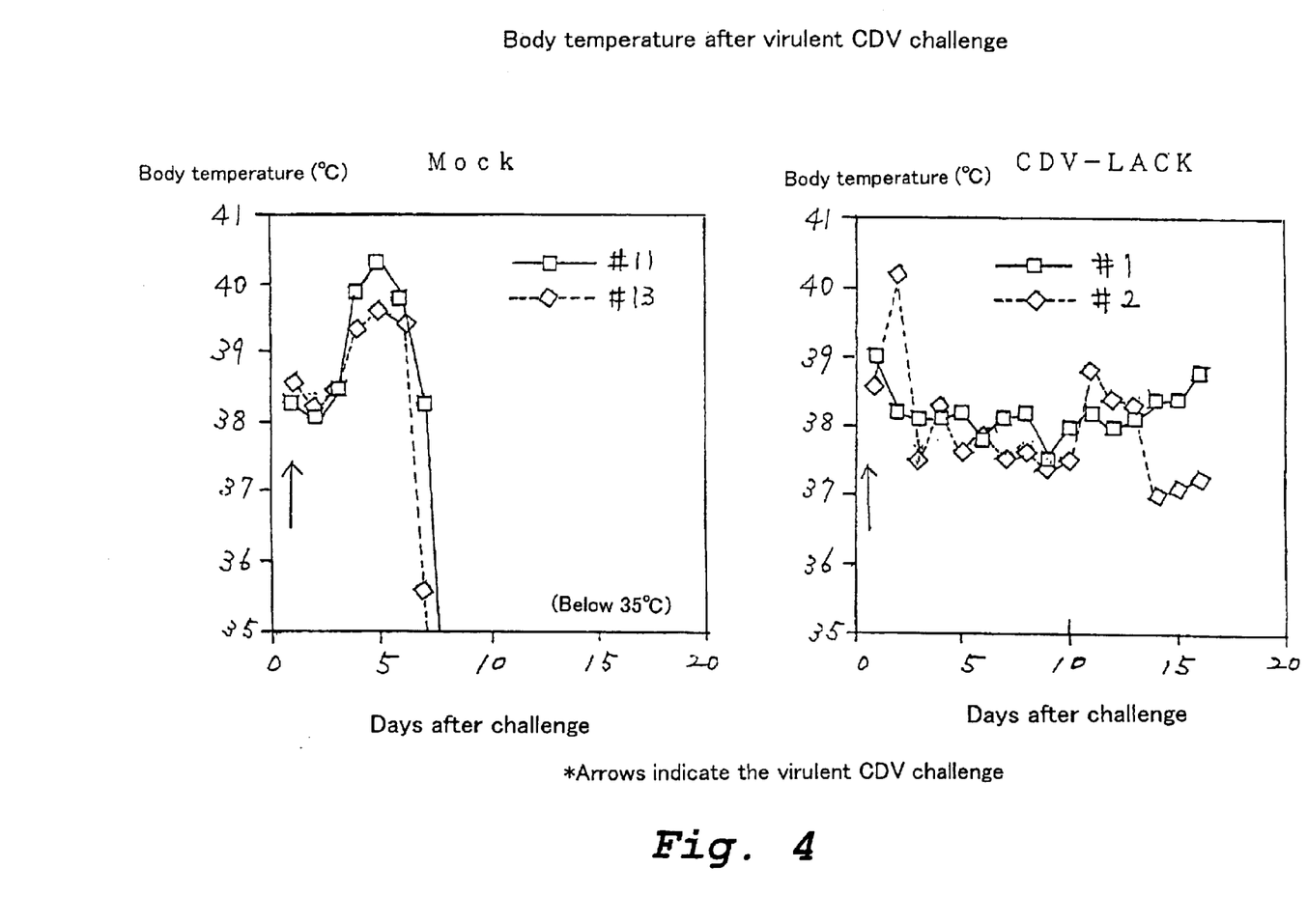
FIG. 4 shows the change in body temperature of test animals after virulent CDV challenge.

FIG. 4 shows the change in body temperature after the challenge. In mock group the body temperature increased rapidly 4 days after the challenge, exceeded 40° C. on Day 5 (climax), and decreased below 35° C. on Day 7, producing collapse and nervous symptoms. Then, the dogs were euthanized under anesthesia and underwent an autopsy. By macroscopy in autopsy, remarkable swelling in the lymph nodes was observed. On the other hand, in the CDV-LACK inoculated group, the body temperature increased transiently on Day 16, but after that, the temperature became normal and no significant change was found clinically.

From the above, it is apparent that inoculation with CDV-LACK is effective as a vaccine against canine distemper.

Example 4

Protection of Dogs against Leishmania Protozoa Propagation in Experimental Vaccination with CDV-LACK The effect of CDV-LACK inoculation on protection against Leishmania protozoa propagation was examined as follows.

Leishmania infection experiments were conducted on 4-week old beagles. Two dogs in a CDV-LACK inoculated group were inoculated with $10^{4.5}$ $TCID_{50}$ of the viruses, and two dogs in a mock group were given 500 µl of PBS subcutaneously. After two weeks, a second inoculation was carried out in the same way as the first inoculation. On Week 8 after the first inoculation, the dogs were challenged with a strain of Leishmania protozoa (*L. major*) in the stage of infection at a dose of $5 \times 10^7/50$ µl at each of four sites on the ears, one site on the nose, and one site on the interdigits. The propagation of Leishmania was evaluated based on the size of nodules.

Figure 5:
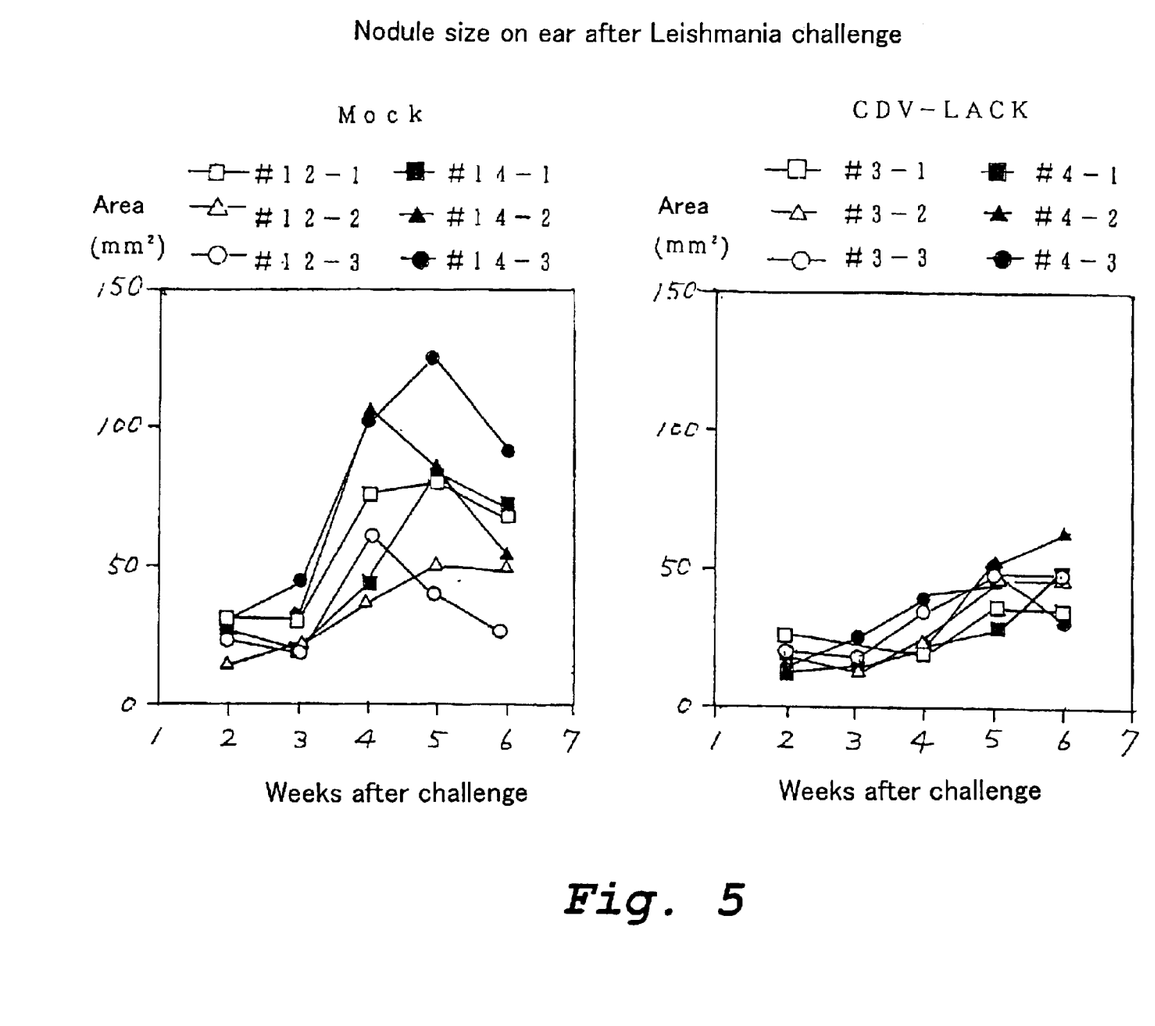
FIG. 5 shows the change of nodule size on ears after Leishmania challenge.

FIG. 5 shows the change of nodule size on the ears from two weeks to six weeks after the challenge.

In the mock group, the nodules became bigger with a peak on Week 4 or 5, and crater-like dimples were observed, indicating rapid propagation of the protozoa. On the other hand, in the CDV-LACK inoculated group, the size of the nodules did not increase remarkably and crater-like dimples were not found. This indicates that the propagation of Leishmania protozoa was suppressed at least until Week 6.

Thus, it was demonstrated that canine distemper virus having the LACK gene inserted as prepared in Example 1 (CDV-LACK) is effective as a bivalent vaccine against canine distemper and leishmaniasis. Namely, CDV-LACK has a vaccine effect on protection against canine distemper by using recombinant canine distemper virus constructed based on a field strain of canine distemper virus, strain Yanaka, which has been isolated recently, and furthermore has a vaccine effect on suppressing the propagation of Leishmania protozoa.

As mentioned above, the present invention provides a recombinant canine distemper virus having a foreign gene involved in the protection against Leishmania protozoa infection inserted into canine distemper virus vector.

This recombinant canine distemper virus has protective effects against both canine distemper and leishmaniasis, thereby providing a bivalent vaccine against these infectious diseases.

What is claimed is:

1. An attenuated recombinant canine distemper virus, comprising a gene that encodes a an immunogenic protein against leishmaniasis, wherein said gene is selected from a group consisting of LACK (Leishmania homologues receptors for activated C kinase) gene, A2 gene, gp63, TSA gene, LmSYII gene of Leishmania protozoa, and PSA-2 of Leishmania protozoa, and wherein said gene is inserted into the canine distemper virus genome at a site between the N gene and P gene of canine distemper virus genes.

2. The attenuated recombinant canine distemper virus according to claim 1, wherein said virus expresses an immunogenic protein that against leishmaniasis.

* * * * *

UNITED STATES PATENT AND TRADEMARK OFFICE
CERTIFICATE OF CORRECTION

PATENT NO. : 6,773,710 B2  
DATED : August 10, 2004  
INVENTOR(S) : Kai et al.

Page 1 of 1

It is certified that error appears in the above-identified patent and that said Letters Patent is hereby corrected as shown below:

<u>Column 9,</u>  
Line 3, "a an immunogenic" should read -- an immunogenic --

<u>Column 10,</u>  
Line 5, "protein that against" should read -- protein against --

Signed and Sealed this

Nineteenth Day of April, 2005

JON W. DUDAS  
*Director of the United States Patent and Trademark Office*